US006025373A

United States Patent [19]
Anderson

[11] Patent Number: 6,025,373
[45] Date of Patent: *Feb. 15, 2000

[54] METHODS FOR REDUCING FIBRINOGEN

[75] Inventor: Pamela Wang Anderson, Indianapolis, Ind.

[73] Assignee: Eli Lilly and Company, Indianapolis, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 09/056,991

[22] Filed: Apr. 8, 1998

Related U.S. Application Data

[60] Provisional application No. 60/044,591, Apr. 22, 1997.

[51] Int. Cl.⁷ .......................... A61K 31/445; A61K 31/38

[52] U.S. Cl. ........................................... 514/324; 514/422

[58] Field of Search ..................... 514/324, 422

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 424/267 |
| 5,075,321 | 12/1991 | Schreiber | 514/317 |
| 5,441,965 | 8/1995 | Sall et al. | 514/324 |
| 5,445,941 | 8/1995 | Yang | 435/6 |
| 5,476,862 | 12/1995 | Calnek et al. | 514/324 |
| 5,482,949 | 1/1996 | Black et al. | 514/324 |
| 5,508,292 | 4/1996 | Sall et al. | 514/324 |
| 5,731,328 | 3/1998 | Berg et al. | 514/324 |

FOREIGN PATENT DOCUMENTS

| | | |
|---|---|---|
| 652 004 A1 | 10/1994 | European Pat. Off. . |
| 659 427 A1 | 12/1994 | European Pat. Off. . |
| 664 126 A1 | 12/1994 | European Pat. Off. . |
| 724 879 A2 | 2/1996 | European Pat. Off. . |
| WO93/10113 | 5/1993 | WIPO . |
| WO93/1704 | 6/1993 | WIPO . |
| WO 97/13511 | 10/1996 | WIPO . |

OTHER PUBLICATIONS

R. Fuchs–Young et al., "Raloxifene is a Tissue–Selective Agonist/Antagonist That Functions through the Etrogen Receptor", Annals of the New York Academy of Sciences, 761:355–60, 1995.

Walsh et al., "Effects of Raloxifene on Serum Lipids and Coagulation Factors in Healthy Postmenopausal Women", JAMA 279:18 1998.

"First Phase III Results With Raloxifene" Database Dialog File 129: Phind Accession & Scrip 2240, 1997.

"Raloxifene Lilly Recommended for Approval" Database Dialog File 445: IMS World R7D Focus, Xp002074925 & R&D Focus Drug News, 1997.

"Raloxifene Lilly Clinical Data" Databse Dialog File 445: IMS World R&D Focus, Xp002074926 & R&D Focus Drug News, Jun. 1997.

D. Somjen et al., "Tissue Selective Action of Tamoxifen Methiodide, Raloxifene and TAmoxifen on Creatine Kinase B Activity In Vitro and In Vivo", J. Steriod Biochem. Molec. vol. 59:5/6:389–396, 1996.

Zukcerman et al., "Inhibition of LDL oxidation and myleoperoxidase dependent tyrosyl radical formation by the selective estrogen receptor modulator raloxifene (LY139481 HCL)" Atherosclerosis 126:65–75, 1996.

Draper et al., "A Controlled Trial of Raloxifene (LY139481) HCI: Impact on Bone Turnover and Serum Lipid Profile in Helathy Postmenopausal Women", Journal of Bone and Mineral Research, 11:16, 1996.

Grey, et al., "The Effect of the Anti–Estrogen Tamoxifen on Cardiovascular Risk Factors in Normal Postmenopausal Women", Journal of Clinical Endocrinology and Metabolism, 80:11, 1995.

Draper et al., "Effects of Raloxifene (LY139481 HC1) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sept. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Min. Res., Tampa, Sep. 18–22, 1993.

Glasebrook et al., "Multiple Binding Sites for the Anti–estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti–Estrogen, Simulates the Effects of Estrogen in Inhibiting Bone Resorption Through Regulating TGFB–3 Expression in Bone;".Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

(List continued on next page.)

*Primary Examiner*—Phyllis G. Spivack
*Attorney, Agent, or Firm*—William R. Boureaux; James J. Sales

[57] ABSTRACT

The invention is related to reducing fibrinogen in a human by administering a 2-aroyl-3-arylbenzo[b]thiophene compound.

6 Claims, No Drawings

OTHER PUBLICATIONS

Black et al., "Evidence for Biological Action of the Antiestrogens LY117018 and Tamoxifen by Different Mechanisms," Endocrinology 109;1981, 987–989.

Black, L.J. "Biological Actions and Binding Properites of a New Estrogen Antagosist LY117018," In: Homone Antagonists, 129–82, 1982 (M.K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, June 8–10, 1983, abs. 93.

Black et al., Antogonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl) ethoxyl]–phenyl] methanone, methanesulfonic acid salt, Journal of Medicinal Chemistry 22;1979, 962–966.

Dina M. Bitar et al., Suppression of Experimental Autoimmune Encephalomyelitis by the Oral Administration of Myelin Basic Protein, Cellular Immunology 112, 364–370, 1988.

Paul J. Higgins, et al., Suppression of Experimental Autoimmune Encephalomyelitis by Oral Administration of Myelin Basic Protein and its Fragments, The Journal of Immunology, vol. 140(2), 440–445, Jan. 15, 1988.

Oral Tolerance to Myelin Basic Protein and Natural Recovery from Experimental Autoimmune Encephalomyelitis Are Associated with Downregulation of Inflammatory Cytokines and Differential Upregulation of Transforming Growth Factor β, Intrerleukin 4, and Prostaglandin E Expression In the Brain, J. Exp. Med., vol., 176, 1355–1364, Nov. 1992.

C.D. Jones, et al. Antiestrogens. 2.[1] Structure–Activity Studies in a Series of 3–Aroyl–2–arylbenzo{b}thiophene Derivatives Leading to [6–Hyddroxy–2–(4–hydroxyphenyl)benzo{b}thien–3–yl] [4–[2–(1–piperidinyl)ethoxy]–phenyl]methanone Hydrochloride (LY156758), A remarkably Effective Estrogen Antagonist With Only Minimal Intrinsic Estrogenicity, J. Med. Chem., 1984, 27, 1057–1066.

A Hendrick, et al., Tamoxifen and Thromboembolism, Journal of the American Medical Association, vol. 243, No. 6, Feb. 8, 1980.

Radwanska, E., The Role of Reproductive Hormones in Vascular Diseases and Hypertension, Steriods, 58(12), 605, Dec. 1993.

Pfilger, et al., Acta Med. Austriaca, 18(3), 68–72, 1991.

METHODS FOR REDUCING FIBRINOGEN

FIELD OF THE INVENTION

This Application claims the benefit of U.S. Provisional Application Ser. No. 60/044,591, filed Apr. 22, 1997.

The current invention relates to the fields of medicinal chemistry, pharmacology, and clinical medicine dealing with the blood coagulation (clotting) system in humans.

BACKGROUND OF THE INVENTION

Coagulation is a result of a complex system which controls the formation of matrix proteins. These matrix proteins, along with other elements such as platelets, form a barrier which is able stop the transport of vital body fluids, especially blood. Traumatic damage to the vasculature causing bleeding, is controlled by the coagulation system and a failure of this system can result in serious and life-threatening situations, such as hemophilia. However, there are many situations; when the coagulation system may be inappropriately activated resulting in a blockage of the flow of vital fluids, such as blood, and causing severe damage to the effected tissues. Some examples of pathologies related to inappropriate and pathological coagulation include pulmonary embolism, myocardial ischemia, myocardial infarction, cerebral thrombosis, stroke, local hypercoaguable caused by inflammation, syndromes related to disseminated intravascular coagulation, and the like. Thus, there is need for a constant balance and control of the coagulation system to maintain homeostasis and good health.

Fibrinogen is a 3.4 KD dimeric protein found in the blood circulation and in other fluids of the body. This protein is the source or reservoir of the protein fibrin. Fibrin is the main building block for the matrix which forms clots in the circulatory system.

In the coagulation system, fibrinogen is converted to soluble fibrin by the enzyme, thrombin. Thrombin production from its precursor, prothrombin, is controlled by a complex series of protein interactions which are known as the intrinsic and extrinsic coagulation systems. The soluble fibrin, produced by the action of thrombin on fibrinogen, is further converted in an insoluble form by the action of factor XIIIa. This resulting insoluble fibrin forms the matrix which along with other elements such as platelets, causes a clot or thrombus to form, thus stopping the flow of blood. (For further details on the coagulation system, see: "Goodman and Gilman's, The Pharmacologic Basis of Therapeutics", Eds. Gilman A. G., Goodman, L. S., and Gilman, A., 6th Ed., Macmillan Publishing Co., NYC, 1980, Chap. 58; "Harrison's Principles of Internal Medicine", Eds. Isselbacher, Adams, Braunwald, Petersdorf, and Wilson, 9th Ed., McGraw-Hill Book Co. NYC, 1980, Chap. 54; and references cited therein).

Today, there are many therapeutic agents which are useful in controlling the coagulation system. Each of these agents, while often effective in preventing or treating inappropriate coagulation, have undesirable side-effects which limit their utility. Examples of agents which prevent coagulation include: 1) Heparin, a glycosaminoglycan polymer, blocks several of the coagulation factors resulting in a decreased conversion of prothrombin to thrombin. This agent must be given by injection and, being a heterogeneous mixture, control of its action is often difficult. 2) The coumarins and indan-1,3-diones, e.g., warfarin, dicumarol, phenindione, etc., affect the vitamin K dependent clotting factors. Although these agents are effective and orally available, they are often too effective in that great care must taken to limit potential uncontrolled bleeding, which may lead to an excess morbidity of mortality.

In addition, there are also agents which treat blood clots which have already formed, and agents which destroy unwanted clots as they form. These agents act by a different mechanism than those described, supra, these agents activate the conversion of plasminogen to plasmin, which in turn hydrolyze fibrin, thus dissolving the formed or forming clot. These agents are known as thrombolytic agents, and include streptokinase, urokinase, and plasminogen activator. These agents are very expensive and must be given by injection, thus limiting their utility for prevention.

Each of these agents suffers from the one common side-effect related to their mechanisms of action which limits their utility. The propensity to be too effective in either preventing clot formation or hydrolyzing those clots which are necessary, or, in other words, offering too narrow a therapeutic index, is a common problem all for these agents and presumably for others operating by similar mechanisms. Thus, most of the commonly used agents are contra-indicated in patients undergoing surgery, biopsy, CPR, or procedures involving the use of a catheter or with factors which dispose them to risk of hemorrhage. Such factors include ulcers, wounds, hypertension, infections, previous stroke, and the like.

The narrow therapeutic index of the known anti-coagulants and thrombolytics is problematic in common situations where a better controlled level of anti-coagulation would be useful. For example, surgeons often face a dilemma when a patient needs surgery, while also requiring anti-coagulant therapy. A patient suffering from cardiac ischemia may need by-pass surgery and clot formation would be necessary in the healing of the surgery, yet inappropriate clots may cause more ischemia and possible infarction.

Additionally, currently available agents pose potential problems when used to prevent inappropriate coagulation, ducts their propensity to become pathologically hypocoagulatory, and this makes them unpredictable and possibly dangerous in long term use.

For example, patients who are treated with current agents to prevent ischemia, such as cerebral stroke, are at risk of hemorrhage if they have a trauma such as a fall or break a bone.

Clearly, it would be of great value to medicine if an agent were available which would not block or destroy useful clotting, but rather lower the clotting threshold in order to lower the risk of inappropriate and pathological clotting.

Estrogen is known to lower the levels of fibrinogen in humans. It is also known that estrogen exerts a very significant protective effect on the cardiovascular system. There is considerable controversy as to the exact mechanism by which estrogen exerts its protective effects. Use of estrogen for the treatment of excess coagulation has not been thoroughly investigated due to its undesirable side-effects. These side effects are on the sex tissues in men or the threat of uterine or breast cancer in women. However, recent studies have shown a relationship between the use of estrogen in post-menopausal women and a reduction in myocardial infarction, an inappropriate coagulation sequelae. An agent which would have the ability to inhibit inappropriate coagulation such as estrogen, but without its side-effects, would have a great potential for use in human medicine.

In addition to fibrinogen's well documented role in the coagulation cascade, fibrinogen has been implicated as a factor in several other pathologies. Fibrinogen and fibrin are found in the synovial fluid of joints which are inflamed.

Fibrinogen and fibrin have been associated with neoplastic metastasis. Decreasing fibrinogen levels in these conditions, without undo hypo-coagulation, may be useful.

SUMMARY OF THE INVENTION

The current invention relates to methods for the reduction of fibrinogen levels a human comprising administering to a human in need thereof an effective amount of compound of formula I:

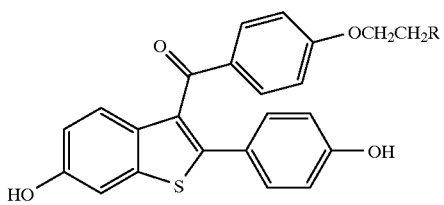

wherein:
R is N-pyrrolidinyl or N-piperidinyl;
or a pharmaceutically acceptable salt or solvate thereof.

DETAILED DESCRIPTION OF THE INVENTION

The current invention is related to the discovery that a select group of 2-aryl-3-aroylbenzo[b]thiophenes, the compounds of formula I, ire useful for decreasing fibrinogen levels in humans.

The term, "pharmaceutically acceptable salt", refers to either acid or base addition salts which are known to be non-toxic and are commonly used in the pharmaceutical literature. Commonly used acid addition salts include: inorganic salts formed by the addition of sulfuric acid, nitric acid, hydrochloric acid, hydrobromic acid phosphoric acid, phosphorous acid and the like; or organic salts formed by the addition of acetic acid, formic acid, benzoic acid, citric acid, methanesulfonic acid and the like. Commonly used basic addition salts are the salts formed by alkali or alkaline earth hydroxides, ammonium hydroxide, alkyl or aromatic amines and the like. A preferred salt of this invention would be the hydrochloride.

A preferred embodiment of this invention is the hydrochloride salt of a compound of formula I where R is N-piperidinyl. This compound, Raloxifene, is named [2-(4-hydroxyphenyl)-6-hydroxybenzo[b]thien-3-yl][4-[2-(1-piperidinyl) ethoxy]phenyl]methanone hydrochloride.

The compounds used in the methods and formulations of the current invention can be made according to procedures, such as those detailed in U.S. Pat. No. 4,133,814 and U.S. Pat. No. 4,418,068, which are included by reference herein. In general, the process starts with a benzo[b]thiophene having a 6-hydroxyl group and a 2-(4-hydroxyphenyl) group. The starting compound is protected, acylated with 4-[2-(1-piperidinyl) ethoxy]benzoyl or 4-[2-(1-pyrolidinyl) ethoxylbenzoyl, and de-protected to form the compounds of formula I.

Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate and solid polyethyl glycols. Final pharmaceutical forms may be pills, tablets, powders, lozenges, syrups, aerosols, saches, cachets, elixirs, suspensions, emulsions, ointments, suppositories, sterile injectable solutions, or sterile packaged powders, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made From polymeric substances or waxes.

The particular dosage of a compound of formula I, required to reduce fibrinogen, or to treat, inhibit, or prevent the sequelae of a patient suffering from inappropriate coagulation by lowering the levels of fibrinogen, is dependent on factors as severity, route of administration, and frequency of dosing and is best decided by the attending physician. Generally, accepted and effective doses will be from 10 mg to 800 mg, and more typically between 20 mg and 100 mg. Such dosages will be administered to a patient in need of treatment from once to three times each day or as often as needed. A preferred dosage would be 60 mg per day via the oral route.

The formulations which follow are given for purposes of illustration and are not intended to be limiting in any way. The total active ingredients in such formulations comprises from 0.1% to 99.9% by weight of the formulation. The term, "active ingredient" means a compound of formula I, preferably Raloxifene.

Formulation 1: Gelatin Capsules

| Ingredient | Quantity (mg/capsule) |
| --- | --- |
| Active Ingredient | 50–600 |
| Starch NF | 0–500 |
| Starch flowable powder | 0–500 |
| Silicone fluid 350 centistrokes | 0–15 |

The ingredients are blended, passed through a No. 45 mesh U.S. sieve, and filled into hard gelatin capsules.

Formulation 2: Tablets

| Ingredient | Quantity (mg/tablet) |
| --- | --- |
| Active Ingredient | 60 |
| Starch | 10–50 |
| Cellulose, microcrystalline | 10–20 |
| Polyvinylpyrrolidone (as 10% solution in water) | 5 |
| Sodium carboxymethyl cellulose | 5 |

-continued

| Ingredient | Quantity (mg/tablet) |
|---|---|
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethyl cellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
|---|---|
| Active Ingredient | 0.50 |
| Ethanol | 29.50 |
| Propellant 22 (Chlorodifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
|---|---|
| Active ingredient | 250 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension

Suspensions each containing 100 mg of a compound of formula I per 5 mL dose.

| Ingredient | Weight |
|---|---|
| Active Ingredient | 100 mg |
| Sodium carboxymethyl cellulose | 50 mg |
| Syrup | 1.25 mL |
| Benzoic acid solution (0.1 M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the entire mixture to the required volume.

The following demonstration of the current invention is for purposes of illustration and should not be construed as limiting the scope of the invention in any way.

Three hundred and ninety, healthy, post menopausal women were randomized into four groups. One group received a placebo, one group received hormone replacement therapy(HRT) (conjugated equine estrogens (Premarin) @ 0.625 mg/day, and 2.5 mg of medroxyprogesterone acetate (Provera) @ 2.5 mg/day), one group received Raloxifene hydrochloride (formula I, where R is N-piperidinyl) @ 60 mg/day, and one group received Raloxifene hydrochloride @ 120 mg/day. All groups were dosed by the oral route. Prior to the initiation of therapy each patient's baseline fibrinogen level was determined. Fibrinogen levels were determined at 6 months of therapy. The results are presented as the median percentage decrease in fibrinogen at the end point of therapy compared to the levels at the beginning. The results of this clinical experience are summarized in Table 1. It was also noted that all therapeutic groups experienced no extraordinary events of inappropriate bleeding, nor any significant pathologic side-effects.

TABLE 1

| Therapy Group | Percent Decrease |
|---|---|
| Placebo | −2.05 |
| HRT | −2.82 |
| Raloxifene @60 mg | −12.18[a,b] |
| Raloxifene @120 mg | −13.05[a,b] |

[a]$p<0.05$ compared to placebo
[b]$p<0.05$ compared to HRT

I claim:

1. A method of reducing fibrinogen in a human comprising the ministration, to a human in need thereof, a compound of formula I

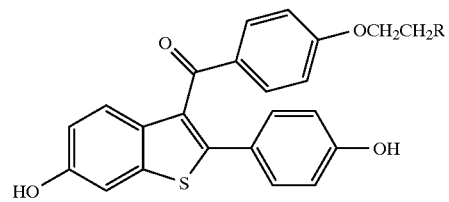

wherein R is N-pyrrolidinyl or N-piperidinyl;
or a pharmaceutically acceptable salt or solvate thereof.

2. A method according to claim 1 wherein R is N-piperidinyl.

3. A method according to claim 2 wherein said compound is the hydrochloride salt thereof.

4. A method according to claim 1 wherein said human is a female.

5. A method according to claim 4 wherein said female is post-menopausal.

6. A method according to claim 1 wherein the dose administered is 60 mg/day via the oral route.

* * * * *